(12) United States Patent
Gilbertson

(10) Patent No.: US 6,905,515 B1
(45) Date of Patent: Jun. 14, 2005

(54) JUNCTION FOR A MODULAR IMPLANT

(75) Inventor: Leslie N. Gilbertson, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 0 days.

(21) Appl. No.: 10/748,824

(22) Filed: Dec. 27, 2003

(51) Int. Cl.⁷ .................................. A61F 2/32
(52) U.S. Cl. ............. 623/22.4; 623/22.42; 623/23.352; 623/23.46
(58) Field of Search .......................... 623/22.11, 22.4, 623/22.41, 22.42, 22.43, 23.14, 23.15, 23.35, 623/23.46, 23.44, 23.43

(56) References Cited

U.S. PATENT DOCUMENTS

| 5,035,717 | A | * | 7/1991 | Brooks .................... 623/23.44 |
| 5,116,379 | A | * | 5/1992 | McLardy-Smith ....... 623/22.42 |
| 5,580,352 | A | * | 12/1996 | Sekel ...................... 623/22.46 |
| 6,090,146 | A | | 7/2000 | Rozow et al. .......... 623/22.42 |
| 6,238,435 | B1 | | 5/2001 | Meulink et al. ......... 623/22.12 |
| 6,330,845 | B1 | | 12/2001 | Meulink .................... 81/462 |

* cited by examiner

Primary Examiner—Bruce E Snow
(74) Attorney, Agent, or Firm—Cary Reeves; Jonathan Feuchtwang

(57) ABSTRACT

The present invention provides an improved junction for modular implant components.

8 Claims, 3 Drawing Sheets

JUNCTION FOR A MODULAR IMPLANT

BACKGROUND

Medical implants to replace or augment various parts of the mammalian body have been successfully used to reduce pain and improve function. For example, orthopaedic implants for replacing portions of bones and joints damaged by disease and/or trauma often eliminate pain and/or increase mobility. Orthopaedic implants for hips, knees, shoulders, ankles, elbows, wrists, the digits of the hands and feet, vertebral bodies, spinal discs, and other bones and joints have been developed. Many medical implants are made more versatile by providing them as separate modular components that can be combined to form an implant suited to a particular patient's condition. Where such modular components are supplied, a means for attaching them to one another is provided.

SUMMARY

The present invention provides a junction for modular implant components.

In one aspect of the invention, a modular joint implant includes a male/female junction between first and second joint components. The first component includes a bore having a longitudinal junction axis and a bore opening. The second component includes a projection engageable with the bore in male/female seating arrangement. A first portion of the bore opening is offset axially relative to a second portion of the bore opening.

In another aspect of the invention, the first portion is offset in a direction of increasing stiffness of the wall surrounding the bore.

In another aspect of the invention, the first portion is offset in a direction of increasing wall thickness.

In another aspect of the invention, the first portion is offset on a side of the implant that is generally in tension when the implant is loaded.

In another aspect of the invention, a modular joint implant includes a male/female junction having a side that is predominately in compression in use and a side that is predominately in tension in use. The implant includes a first component including a bore having a bore opening and an interior surface forming a female side of the male/female junction. The first component further has an exterior surface. The interior and exterior surfaces define a wall between them having a wall thickness. The wall thickness on the tensile side of the implant being greater than the wall thickness on the compressive side of the implant.

In another aspect of the invention, a modular joint implant includes a male/female junction having a side that is predominately in compression in use and a side that is predominately in tension in use. The implant includes a first component including a bore having a bore opening and an interior surface forming a female side of the male/female junction. The bore has a side on the tensile side of the implant that is shifted axially relative to a side of the bore on the compressive side of the implant.

These and other aspects of the invention will be described in reference to the appended drawings.

BRIEF DESCRIPTION OF THE DRAWINGS

Various embodiments of the present invention will be discussed with reference to the appended drawings. These drawings depict only illustrative embodiments of the invention and are not to be considered limiting of its scope.

DESCRIPTION OF THE ILLUSTRATED EMBODIMENTS

Embodiments of a junction for a modular implant are applicable to a variety of implants for use throughout the body. A femoral hip stem has been used to illustrate the invention. However, the invention may also be applied to various other implants including orthopaedic implants for hips, knees, shoulders, ankles, elbows, wrists, the digits of the hands and feet, vertebral bodies, spinal discs, and other suitable implants.

Figure 1:
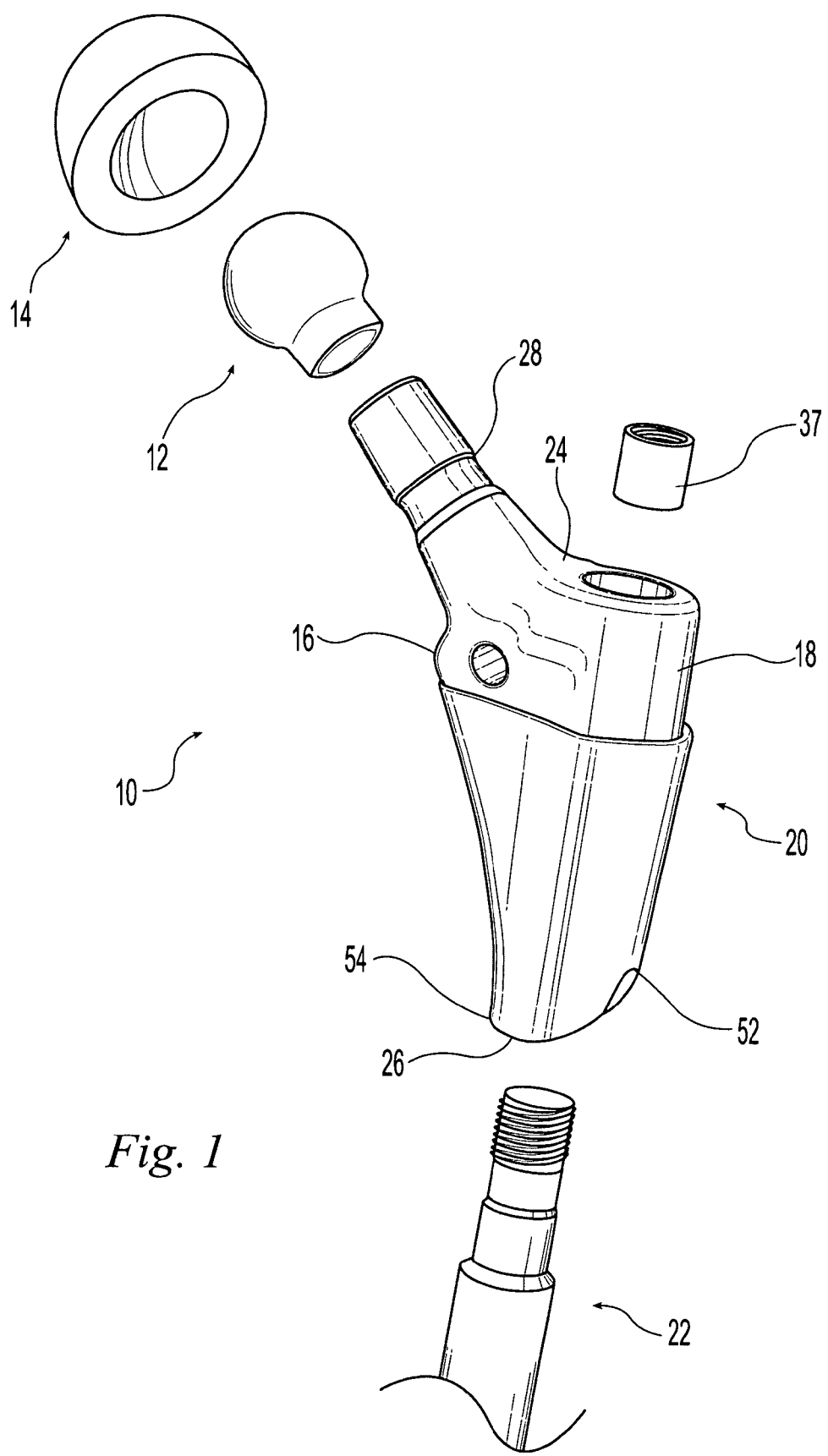
FIG. 1 is an exploded perspective view of a modular implant junction according to the present invention.
Figure 2:
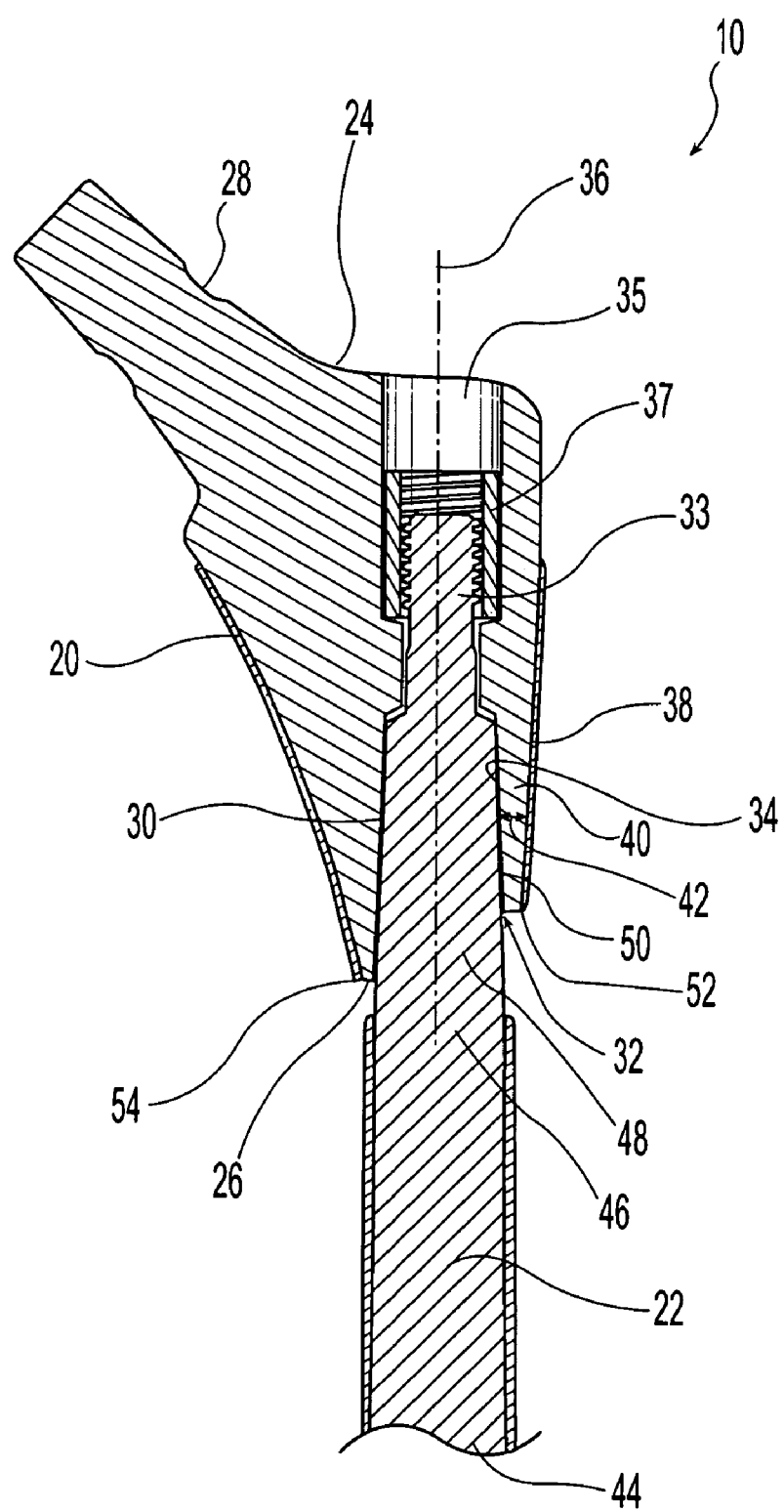
FIG. 2 is a side section view of the modular implant junction of FIG. 1.

FIGS. 1–2 depict a modular femoral hip implant 10 for replacing the proximal head and neck of a femur of a hip joint that has been damaged due to injury or disease. In use, the proximal head and neck are surgically removed and the femoral hip implant 10 is inserted into the proximal femur. The femoral hip implant 10 supports a femoral head 12 that may be a modular and separate component as shown. Optionally, the femoral head 12 may be integral to the femoral hip implant 10. An acetabular component 14 may be implanted in the acetabulum of the pelvis to articulate with the femoral head 12. Optionally, the femoral head 12 may articulate with the natural acetabulum. The femoral hip implant 10 has a medial aspect 16 and a lateral aspect 18. When the patient loads the joint, such as by standing, walking, or other activities, forces are transmitted to the femoral hip implant 10 through the head 12. These forces tend to create a bending moment that places the medial aspect 16 of the femoral hip implant in compression and the lateral aspect 18 in tension.

The femoral hip implant 10 may include modular components such as a proximal body 20 and a stem 22. The proximal body 20 has a top end 24 and a bottom end 26. A neck 28 extends upwardly and medially from the top end 24 to support the femoral head 12 for articulation with the acetabular component 14. The proximal body 20 and stem 22 include a male/female junction for holding them together. In the illustrative embodiment, the female side of the junction is depicted in the proximal body 20 and the male side of the junction is depicted on the stem 22. It is contemplated that the male/female portions may be reversed and still fall within the scope of the invention. The proximal body 20 includes a bore 30 (FIG. 2) having a bore opening 32 and an interior surface 34 forming the female side of the male/female junction. The bore 30 has a longitudinal junction axis 36. The proximal body 20 has an exterior surface 38 spaced from the interior surface 34 of the bore 30. The exterior 38 and interior 34 surfaces define a wall 40 between them. The wall 40 has a wall thickness 42 that may be constant or that may increase from the bore opening 32 toward the top end 24 as shown in FIG. 2. An increasing wall thickness may be accomplished by tapering the bore such that it narrows from the bore opening 32 toward the top end 24 as in the illustrative embodiment. A tapered bore can be made self-locking as is known in the art.

The stem 22 includes a bottom end 44 and a top end 46. The bottom end 44 is configured for insertion into the intramedullary canal of the patient's femur. The top end 46 includes a projection 48 having an exterior surface 50 forming the male side of the male/female junction. The projection 48 is engageable with the bore 30 in male/female seating arrangement along the junction axis 36. A threaded stud 33 extends from the projection 48 and is received by a counter bore 35 formed in the proximal body 20. A nut 37 threads onto the stud 33 to secure the male/female junction.

When the femoral hip implant 10 is loaded, the medial aspects of the proximal body 20 and stem 22 are placed in compression and the lateral aspects of the proximal body 20 and stem 22 are placed in tension. Due to differences in the bending stiffness of the proximal body 20 and stem 22 in the region of the male/female junction, the bore wall 40 may move relative to the exterior surface 50 of the projection 48. Cyclic loading can lead to fretting between the interior surface 34 of the bore 30 and exterior surface 50 of the projection 48. This may be more problematic on the tension side since tensile forces may initiate and propagate fatigue cracks.

The magnitude of the fretting motion is related to the relative stiffness of the male and female parts of the junction. The relative motion at the opening 32 of the bore 30 is an accumulation of the relative motion along the entire length of the junction. This accumulated relative motion may be decreased by decreasing the length along which the relative motion accumulates on the tensile side of the junction. However, it is ineffective to simply make the junction shorter, because this will create higher stresses on the smaller diameter male cross section where such a shortened junction would end. However, by shortening only the tensile side, the compressive side is still supported and the tensile stress at the end of the tensile side increases only slightly while the relative fretting motion decreases significantly. In the illustrative embodiment, a lateral portion 52 of the bore opening 32 is offset axially upwardly relative to a medial portion 54. This offset, or relieved, portion 52 can be created by stepping up the lateral portion 52, sloping up the lateral side such that the bore opening 32 is transverse to the junction axis 36, or by forming the bore opening in some other suitable shape.

Fretting in the male/female junction can also be reduced by better matching the stiffness of the male and female sides of the male/female junction. The present investigators have found that one way to better match the stiffness of the male and female sides is to increase the stiffness of the bore wall 40 adjacent the bore opening 32 on the tensile side of the implant 10. Increasing the stiffness can be accomplished by increasing the outer diameter of the proximal body 20 adjacent the bore opening 32 to move material radially away from the junction axis 36 such that the bending moment of inertia is increased. Increasing this stiffness can also be accomplished by increasing the wall thickness of the proximal body 20 at the junction of the proximal body 20 and projection 48. In the illustrative embodiment, the bore 30 is tapered so that it narrows proximally and the wall thickness 42 increases proximally. By offsetting a lateral portion 52 of the bore opening 32 axially upwardly relative to a medial portion 54 the wall thickness on the lateral side 18 of the bore opening 32 is increased. This offset, or relieved, portion 52 can be created by sloping the lateral side such that the bore opening 32 is transverse to the junction axis 36 as shown, by stepping up the lateral portion 52, or by forming the bore opening in some other suitable shape. In the illustrative embodiment, the projection 48 forming the male side of the junction narrows upwardly. Thus, moving the lateral portion 52 upwardly also moves the lateral interface to an area of decreased stiffness of the projection 48 to further match the stiffness of the male and female portions laterally. Finally, by moving the lateral side upwardly while having the medial, anterior, and posterior sides of the junction extend further downwardly, the fatigue properties of the lateral side are improved while the overall interface of the male and female parts is kept relatively large to facilitate secure engagement between them.

Figure 3:
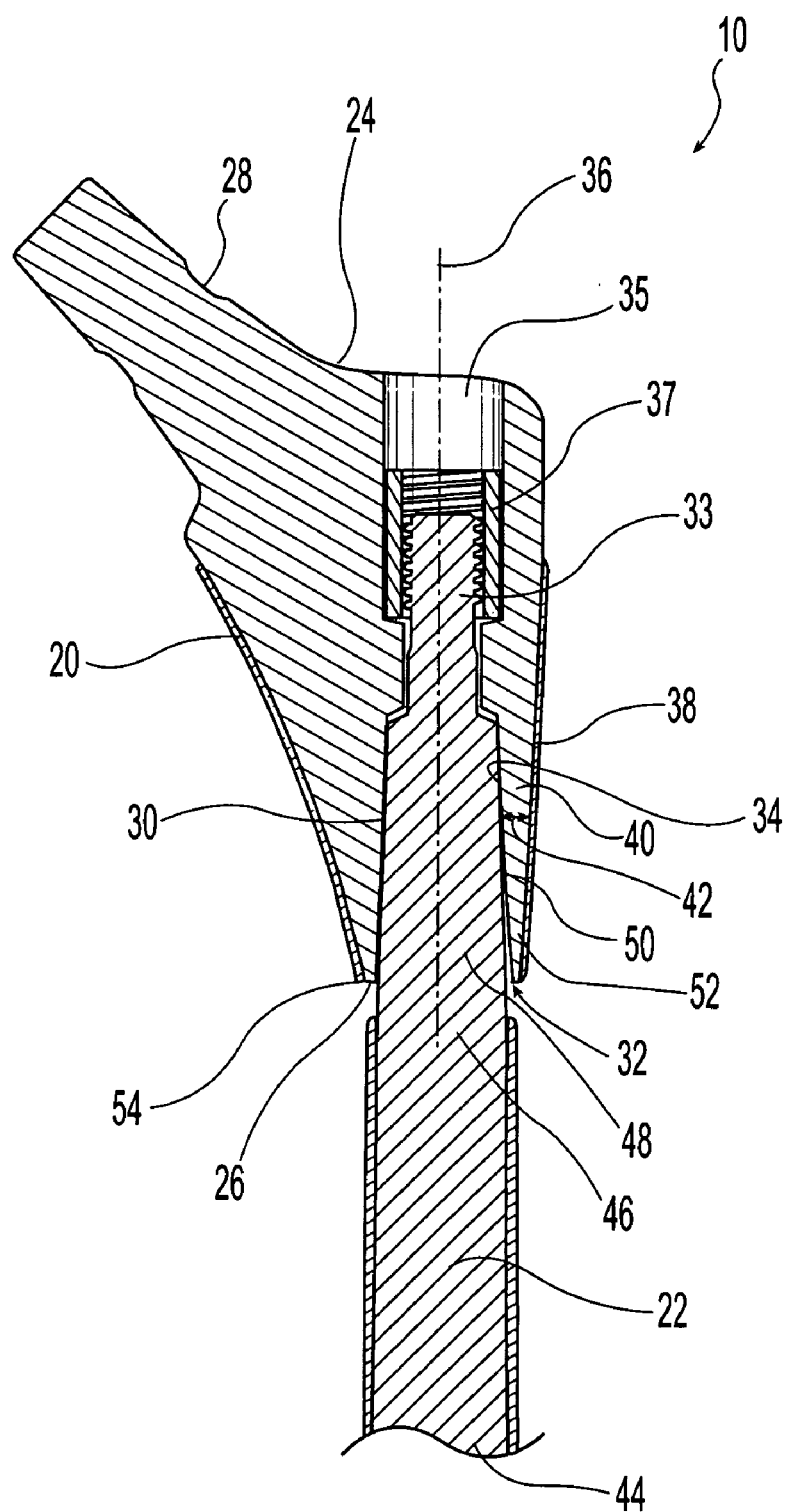
FIG. 3 is a side section view of an optional configuration of the lateral side of the modular implant junction of the present invention.

Another way increase the stiffness of the bore wall 40 is to enlarge the bore 30 on just the tensile side of the junction as shown in FIG. 3 such that the bore wall is offset away from the projection 48. This has the same effect as moving the tensile side axially upwardly as described above. Other ways of better matching the stiffness of the male and female sides of the junction may also be used and are considered within the scope of this invention.

It will be understood by those skilled in the art that the foregoing has described illustrative embodiments of the present invention and that variations may be made to these embodiments without departing from the spirit and scope of the invention defined by the appended claims.

What is claimed is:

1. A modular implant for insertion into a femur adjacent a hip joint, the implant comprising:
   a proximal body component having a top end for engaging the hip joint, a bottom end for insertion into the femur, a medial side, a lateral side, a neck formed adjacent the top end and a bore formed into the bottom end, the bore having a bore opening and an interior surface forming a female side of a male/female junction, the bore having a longitudinal junction axis;
   a stem component having a first end for engaging the proximal body component a second end for insertion into the femur, and a projection formed adjacent the first end, the projection having an exterior surface forming a male side of the male/female junction, the projection being engageable with the bore in male/female seating arrangement along the junction axis, the male and female sides contacting one another adjacent the bore opening, the contact between the male and female sides adjacent to the bore opening on the lateral side being offset longitudinally toward the top end relative to the contact between the male and female sides adjacent the bore opening on the medial side.

2. The implant of claim 1 wherein the bore and the projection form complimentary tapers, the tapers narrowing from the bottom end toward the top end and from the second end toward the first end.

3. The implant of claim 1 wherein the proximal body component has an exterior surface spaced from the interior surface of the bore, the exterior and interior surfaces defining a wall between them, the wall having a wall thickness that increases over a portion of the wall between the bottom end and the top end as the bore taper diverges inwardly from the exterior wall in a direction generally parallel to the junction axis such that the contact between the male and female sides adjacent the bore opening on the lateral side is offset in the direction of increasing wall thickness.

4. The implant of claim 1 further comprising a femoral head component supported on the neck of the proximal body component and an acetabular component engageable with the femoral head component.

5. The implant of claim 1 wherein the bore opening is transverse to the junction axis.

6. The implant of claim 1 wherein the implant further includes a joint load receiving head and further wherein the medial side is generally in compression in use and the lateral side is generally in tension in use such that the contact between the male and female sides adjacent the bore opening is offset longitudinally toward the top end on the tensile side of the implant.

7. The implant of claim 1 wherein the proximal body component has an exterior surface spaced from the interior surface of the bore, the exterior and interior surfaces defining a wall between them, the wall having a stiffness that increases over a portion of the wall between the bottom end and the top end in a direction generally parallel to the junction axis, the projection further having a stiffness, such that the contact between the male and female sides adjacent to the bore opening on the lateral side is offset in the direction of increasing wall stiffness.

8. The implant of claim 1 wherein the bore opening adjacent the lateral side is offset radially away from the projection.

* * * * *